United States Patent [19]

Gilman

[11] Patent Number: 5,090,406
[45] Date of Patent: Feb. 25, 1992

[54] VENTED ABSORBENT DRESSING
[75] Inventor: Thomas H. Gilman, Mansfield, Mass.
[73] Assignee: Alvin Isaacs, Mansfield, Mass.
[21] Appl. No.: 648,067
[22] Filed: Mar. 6, 1991

Related U.S. Application Data

[63] Continuation-in-part of Ser. No. 337,591, Apr. 13, 1989.

[51] Int. Cl.[5] ............ A61F 13/00; A61F 15/00; A61L 15/00
[52] U.S. Cl. ............ 602/47; 128/888; 602/42
[58] Field of Search ............ 128/155, 888; 604/307

[56] References Cited

U.S. PATENT DOCUMENTS

| | | | |
|---|---|---|---|
| 2,443,140 | 6/1948 | Larsen | 128/888 |
| 4,399,816 | 8/1983 | Spangler | 128/888 |
| 4,541,426 | 9/1985 | Webster | 128/156 |
| 5,056,510 | 10/1991 | Gilman | 604/307 |

FOREIGN PATENT DOCUMENTS 2268504  12/1975  France ............ 128/156

*Primary Examiner*—Randall L. Green
*Assistant Examiner*—Paul Prebilic
*Attorney, Agent, or Firm*—Alvin Isaacs

[57] ABSTRACT

A vented dressing is disclosed including a vent cover for providing controlled leakage of fluid from the wound, wherein the vent cover consists essentially of inner and outer sheets secured together in superposition, the inner sheet comprising an elastomeric water-swellable polymeric material, the outer sheet providing a barrier to water evaporation.

10 Claims, 1 Drawing Sheet

VENTED ABSORBENT DRESSING

RELATED APPLICATION

This application is a continuation-in-part of my copending application, Serial No. 337,591 filed Apr. 13, 1989.

BACKGROUND OF THE INVENTION

The aforementioned parent application, Ser. No. 337,591 describes and claims an improved vented wound dressing having a base sheet for contacting the skin of the patient, the base sheet having an opening for placement over the wound. The dressing has a cover sheet secured to the base sheet having vent means for providing controlled leakage of fluid along a path from the wound through the opening in the base sheet while reducing evaporation through the opening and thereby helping to insure a moist environment when excess wound fluid is removed from the wound.

In accordance with the various embodiments disclosed in the aforementioned application, the vent cover sheet may be substantially planar or it may be raised or corrugated.

The flat cover sheets will in general provide entirely satisfactory leakage for a period of time. However, in time they have a tendency to become sealed by drying serum or wound exudate. Accordingly, such a cover design is not optimal for permitting controlled leakage in dressings that are expected to be retained in place and to continue leaking for several days or longer.

Raised or corrugated vent cover sheets, on the other hand, will maintain reliable leakage for appreciably longer periods. However, they tend to be difficult to manufacture and moreover, are not as esthetically pleasing.

The task of this invention, simply stated, is to provide an improved cover sheet which is characterized as being easy to manufacture, esthetically pleasing and which will provide reliable controlled leakage for an extended period of time.

BRIEF DESCRIPTION OF THE INVENTION

In accordance with this invention, this task is solved in an elegant manner by providing a substantially flat vent cover consisting of inner and out sheet materials secured in superposition, the inner sheet comprising an elastomeric water-swellable polymeric material, the outer sheet comprising material which provides a barrier to water evaporation, i.e. inhibits water evaporation.

DETAILED DESCRIPTION OF THE INVENTION

Figure 1:
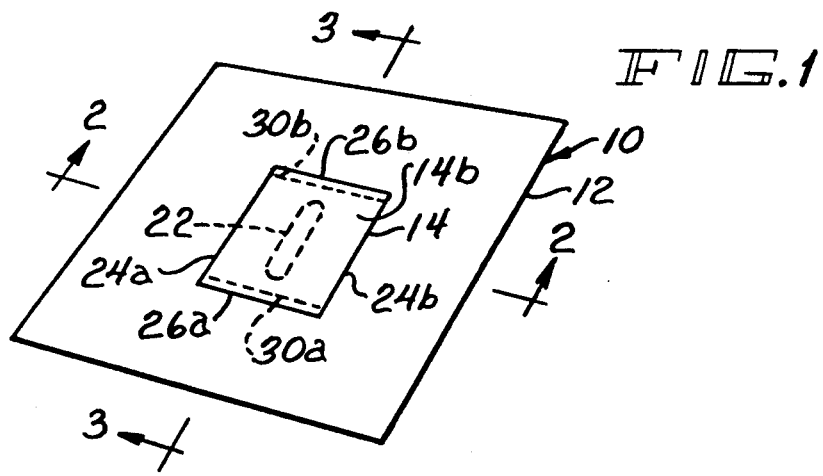
FIG. 1 is a perspective view of a dressing of the present invention.

The accompanying drawing illustrates one embodiment of the present invention and which, with the exception of the cover sheet design (as will be discussed in detail hereinafter) is further illustrative of a parallel embodiment of the invention described and claimed in the parent application, Ser. No. 337,591.

With reference thereto, there is shown a dressing generally designated 10 having a base sheet 12, a vent cover 14, and an absorbent layer 16. The base sheet 12 has an adhesive 18 on a front surface 20 of the base sheet 12 for securing the dressing 10 to the skin S of a patient. Useful adhesives include those per se known in the wound dressing art, e.g. rubber-based, acrylic, vinyl ether and hydrocolloid pressure-sensitive adhesives. As shown, the base sheet 12 has an opening 22 extending therethrough, and the base sheet 12 is secured to the patient with the opening 22 located over a wound W of the patient. The base sheet 12 may be constructed from a suitable moisture vapor permeable elastomer film, such as a polyurethane film.

The vent cover 14 preferably has a generally rectangular shape. The vent cover 14 has a pair of opposed side edges 24a and 24b, and a pair of opposed end edges 26a and 26b connecting the side edges 24a and 24b. As shown, the vent cover 14 is secured to a back surface 28 of the base sheet 12 along sealing lines 30a and 30b, such as adhesive or heat sealing, extending along and adjacent the end edges 26a and 26b. In this configuration, the vent cover 14 covers the opening 22 of the base sheet 12, with the side edges 24a and 24b of the vent cover 14 is being free of attachment from the base sheet 12.

As shown, the absorbent layer 16, such as a gauze sponge, is located over the back surface 28 of the base sheet 12 and over the vent cover 14, and may have dimensions approximately the size of the base sheet 12. The absorbent layer 16 may be secured by suitable tape strips 32 having an adhesive 34 on a front surface thereof to the skin S of the patient. Although the absorbent layer 16 need not have a bacterial barrier, it preferably has a back film 36 of bacteria impervious material, such as the material of the base sheet 12, secured to a back surface 38 of the absorbent layer 16.

In use, the base sheet 12 is secured to the skin S of the patient with the opening 22 located over the wound W, and the absorbent layer 16 is secured over the vent cover 14 by the tape strips 32. This configuration permits passage or migration of excess wound fluid through the opening 22 of the base sheet 12, past the side edges 24a and 24b of the vent cover 14, and then into the absorbent layer 15 where the wound fluids are retained. The vent cover 14 permits leakage in a controlled manner through the opening 22 in order to prevent the undermining of the adhesive seal of the adhesive layer 16 to the skin S of the patient. Also, the vent cover 14, covering opening 22, helps insure a moist environment when excess fluid is wicked away from the wound by absorbent layer 16. It does this by reducing evaporation through opening 22 which would proceed more rapidly if the opening were not covered by the vent sheet. In addition, the film 36 of the absorbent layer 16 prevents the passage of bacteria to the absorbent layer 16 and the wound W. Moreover, since direct contact of the absorbent layer to the wound is obviated by the vent sheet, the dressing 10 prevents adherence of the absorbent layer 16 to the wound W. When the absorbent layer 16 becomes saturated by wound fluids, the tape strips 32 may be removed in order to replace a new absorbent layer 16 after which additional tape strips 32 are utilized to secure the new absorbent layer 16 in place on top of the base sheet 12. Thus, the absorbent layer 16 may be changed without the necessity of removing the base sheet 12 from the skin S of the patient, which would otherwise cause "tape stripping" by repeated removal of the dressing which irritates the skin. Thus, in accordance with the present invention, the dressing maintains a moist wound surface, prevents scab formation, prevents contact between wound fluid and intact skin, thereby protecting the intact skin from maceration.

Although the opening 22 of the base sheet 12 is shown in the illustrative drawing as being elongated it may instead be circular, or of any other suitable shape. It is preferably located centrally between the side edges 24a and 24b and end edges 26a and 26b of the vent sheet 14. Alternatively, the base sheet 12 may have a plurality of openings 22 of any suitable shape located beneath the vent sheet 14.

Figure 2:
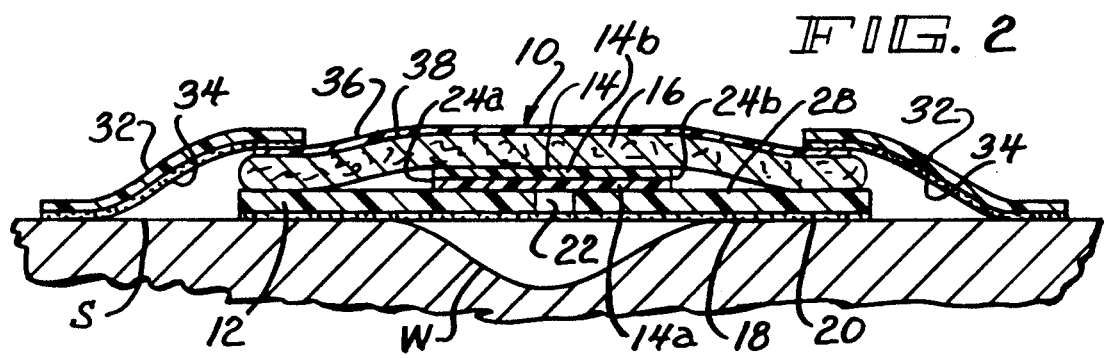
FIG. 2 is a sectional view taken substantially as indicated along the line 2—2 of FIG. 1.
Figure 3:
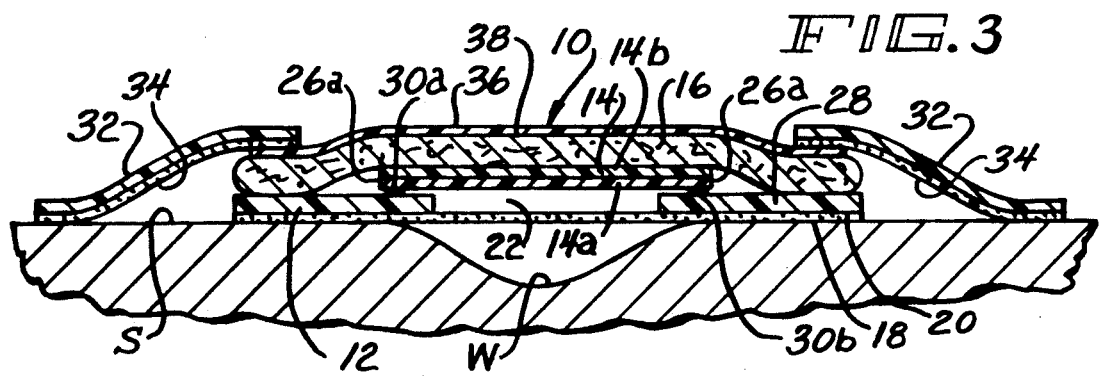
FIG. 3 is a sectional view taken substantially as indicated along the line 3—3 of FIG. 1.

In accordance with the parallel FIGS. 1–3 of the parent case, Ser. No. 337,591, the vent cover 14 consists of a single sheet material, e.g. a suitable elastomer water vapor-permeable material which may be on the order of one mil thick. Suitable materials are said to include "pellethane" (trademark of Upjohn) 236380AE and "Saran" (trademark of Dow Chemical).

However, as previously alluded to, in accordance with the present invention, the vent cover 14 will consist of an inner sheet 14a facing the base sheet 12 and an opposed outer sheet 14b, the sheets 14a and 14b being secured together in superposed relationship.

In accordance with the present invention, inner sheet 14a comprises a water-swellable elastomer, preferably one that will swell at least 20% and most preferably at least 50%. It may be on the order of 1.5 –2.5 mils thick. Suitable water-swellable elastomeric polymeric materials useful in the practice of this invention include nylon/polyethylene oxide block copolymers such as "PEBAX 4011" (trademark of Atochem) and polyester/ polyethylene oxide block copolymers such as "Hytrel 8171"(trademark of DuPont). Other useful materials will be readily suggested to those skilled in the art in the light of the present disclosure.

Outer layer 14b which may for example, be a mil thick or even less, comprises a material which is a barrier to water evaporation. Preferably, layer 14b comprises an elastomeric polymeric material including those which are thermoplastic polymers. Most preferably, the polymeric material is further characterized as being substantially non-water-swellable. Suitable materials of this description include natural rubber, butyl rubber, and synthetic rubbers such as those of the "Kraton" (trademark of Shell Chemical) series. Suitable materials useful for providing the outer layer are per se well known in the art and their selection will also be within the expected judgment of the skilled worker.

Sheets 14a and 14b may be laminated together to provide a laminar cover sheet 14 or they may be sealed in superposed relationship by seal spots or lines, e.g. by continuous seal lines, discontinuous seal lines, or by spot seals around all or a portion of their common periphery. The seals may be provided by heat sealing or by means of a suitable per se known medical grade adhesive, e.g. an acrylic pressure-sensitive adhesive.

By way of recapitulation, the present invention is directed to an improvement in wound dressings of the type described in the parent application, Ser. No. 337,591, comprising a base sheet for contacting the skin of the patient, the base sheet having an opening for placement over the wound; means for securing the base sheet to the skin of a patient; and vent means for providing controlled leakage of fluid along a path from the wound through the opening of the base sheet, the vent means comprising cover means permitting passage of wound fluid therethrough while reducing evaporation through the opening and thereby helping to insure a moist environment when excess wound fluid is removed from the wound; the improvement being employed as the vent cover means inner and outer sheets secured together in superposition, the inner sheet comprising an elastomeric water-swellable polymeric material, the outer sheet comprising a material which is a barrier to water evaporation, preferably an elastomer as described above.

The vent cover means of this invention provides controlled leakage over longer periods of time than does the single sheet vent cover means disclosed in the parent case.

While for purposes of illustration, the vented dressings to which this invention is directed has been shown to contain a single opening 22 in the base sheet 12, as heretofore alluded to, the base sheet may be provided with a plurality of openings 22. In a preferred embodiment of this invention, the base sheet 12 will contain a plurality of openings 22 and in lieu of the dressing having a single vent cover 14, it will contain two or more separate vent covers, each of which provides controlled leakage from one or more of the openings 22. In other words, each of the plurality of openings in the base sheet may have its own separate vent cover to provide the controlled leakage or, alternatively, each vent cover may cover and thus control leakage from two or more of the openings in the base sheet.

Since various modifications may be made without departing from the scope and spirit of the invention herein contemplated, it is intended that all matter in the foregoing description, including the drawing, shall be taken as illustrative and not in a limiting sense.

What is claimed is:

1. In a dressing for a wound of a patient, comprising:
 a base sheet contacting the skin of base sheet having at least one opening for placement over the wound;
 means for securing the base sheet to the skin of a patient; and
 vent means for providing controlled leakage of fluid along a path from the wound through each said opening of the base sheet, said vent means comprising cover means covering said opening, said cover means permitting passage of wound fluid therethrough while reducing evaporation through said opening and thereby helping to insure a moist environment when excess wound fluid is removed from said wound;
 the improvement wherein the cover means comprises inner and outer sheets secured together in superposition, the inner sheet comprising an elastomeric water-swellable polymeric material, the outer sheet comprising a material which provides a barrier to water evaporation.

2. The dressing of claim 1 further including means for preventing bacteria from reaching the wound along said fluid path.

3. The dressing of claim 1 further including means for absorbing the fluid passing from the vent means.

4. A dressing as defined in claim 1 wherein the inner and outer sheets are laminated together.

5. A dressing as defined in claim 1 wherein the outer sheet material is a polymeric material.

6. A dressing as defined in claim 5 wherein the polymeric material is an elastomer.

7. A dressing as defined in claim 5 wherein the polymeric material is substantially non-water-swellable.

8. A dressing as defined in claim 5 wherein the polymeric material is thermoplastic.

9. A dressing as defined in claim 1 wherein the base sheet has a plurality of said openings.

10. A dressing as defined in claim 9 wherein the vent means comprises a plurality of individual cover means, each of the cover means covering at least one of the openings.

* * * * *